United States Patent [19]

Becker

[11] 4,314,480
[45] Feb. 9, 1982

[54] VENOUS PRESSURE ISOLATOR

[75] Inventor: Lawrence F. Becker, Chicago, Ill.

[73] Assignee: Baxter Travenol Laboratories, Inc., Deerfield, Ill.

[21] Appl. No.: 168,471

[22] Filed: Jul. 14, 1980

[51] Int. Cl.³ ............................................... G01L 7/08
[52] U.S. Cl. ....................................... 73/706; 73/714; 73/715; 92/98 R
[58] Field of Search ......................... 73/706, 714, 715; 128/214 E, DIG. 13; 92/98 R

[56] References Cited

U.S. PATENT DOCUMENTS

| 17,607 | 6/1857 | Miller et al. | 73/715 |
|---|---|---|---|
| 2,296,237 | 9/1942 | Allen | 73/715 |
| 2,751,935 | 6/1956 | Smith | 137/795 |
| 3,482,696 | 12/1969 | Jones, Jr. | 210/90 |
| 3,645,139 | 2/1972 | Zavoda | 92/102 |
| 3,713,341 | 1/1973 | Madsen et al. | 73/715 |
| 3,863,504 | 2/1975 | Borsanyi | 73/706 |
| 4,022,190 | 5/1977 | Meyer | 250/336 |
| 4,077,882 | 3/1978 | Gangemi | 92/5 R |
| 4,109,535 | 8/1978 | Reed et al. | 92/102 |
| 4,226,124 | 10/1980 | Kersten | 73/706 |

Primary Examiner—Donald O. Woodiel
Attorney, Agent, or Firm—John P. Kirby, Jr.; John A. Caruso; Paul C. Flattery

[57] ABSTRACT

Apparatus for protecting a pressure-sensitive transducer in an extracorporeal blood system and for providing a sterile barrier while the apparatus transmits the blood pressure to the pressure-sensitive transducer. The apparatus (34) comprises a housing (40, 42) having first (40) and second (42) generally hemispherical members which symmetrically enclose a generally planar silicone membrane diaphragm (44). The membrane diaphragm (44) has a thickness that is less than 0.040 inch and a diameter that is at least twice as great as the intended total deflection distance. The membrane (44) is centered within the housing (40, 42) and greater pressure on either side of the membrane (44) will cause the membrane (44) to deflect to the other side by stretching.

10 Claims, 8 Drawing Figures

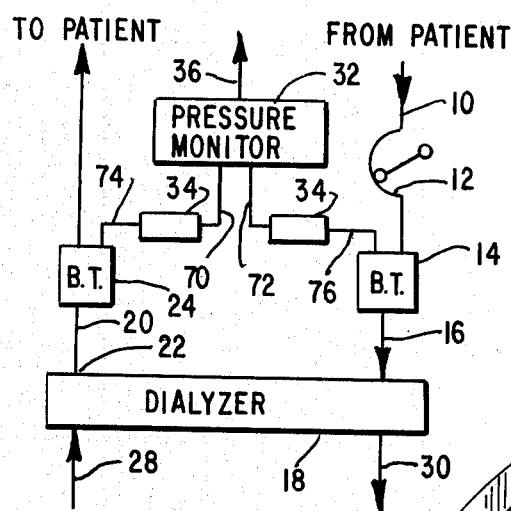
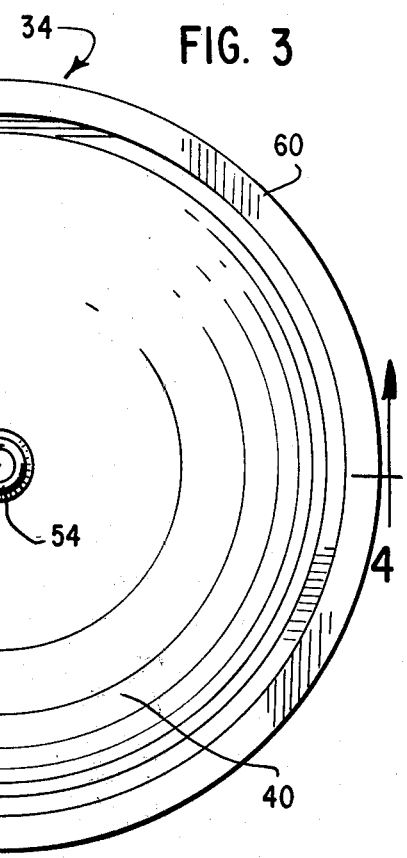
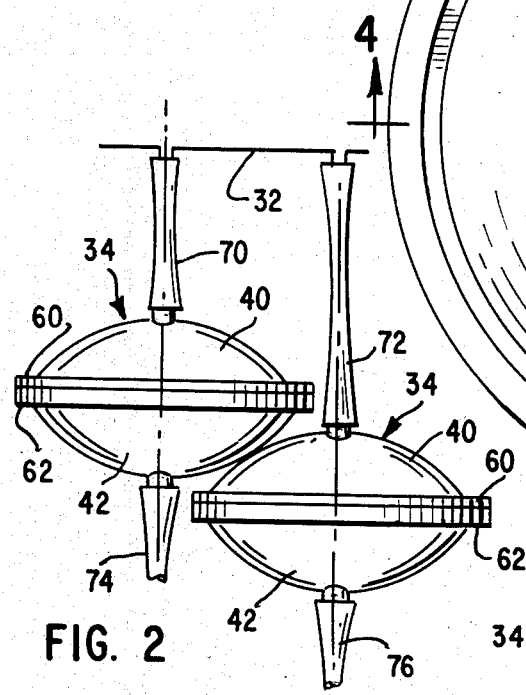
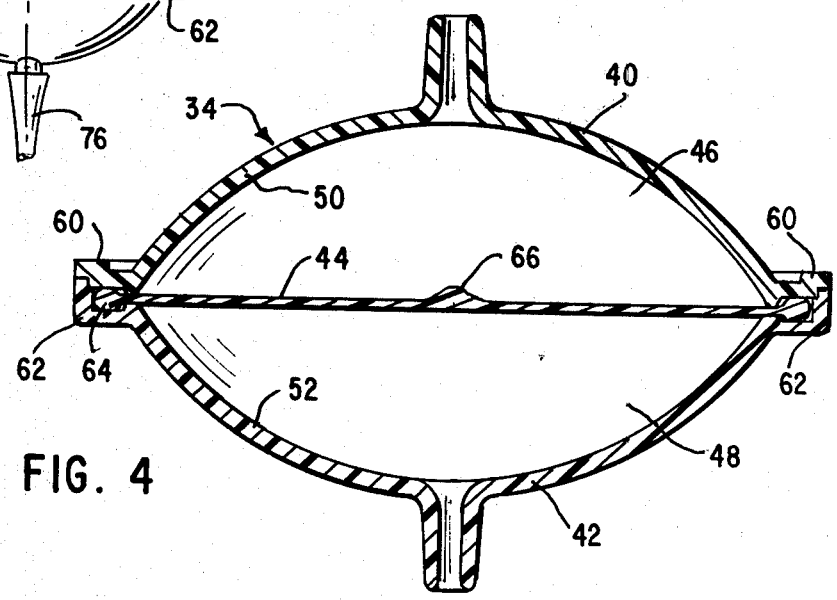

VENOUS PRESSURE ISOLATOR

BACKGROUND OF THE INVENTION

The present invention concerns an improved apparatus for isolating a pressure-sensitive device from blood flowing in an extracorporeal blood system and for transmitting the blood pressure to the pressure sensing device.

In a typical extracorporeal blood system, such as dialysis or oxygenation, for example, blood is pumped from a patient through an administration set which contains a bubble trap, through the mass transfer device (such as the dialyzer or the oxygenator), through another administration set which contains a bubble trap and back to the patient. The blood pressures in the line are typically monitored using one or more pressure-sensitive transducers. The transducers are isolated from the blood flow line by means of an isolating device which may be coupled between the blood flow line and the pressure-sensitive transducer. The isolating device must be operable to protect the transducer, to provide a sterile barrier and to transmit the blood pressure to the transducer.

One type of isolating and blood pressure transmitting device is disclosed in Gangemi U.S. Pat. No. 4,077,882, issued Mar. 7, 1978. I have discovered an isolating device that is superior in construction and operation with respect to the device disclosed in the Gangemi U.S. Patent, in that the present invention is simpler in construction and thus provides manufacturing advantages, has a construction which requires less membrane displacement thus resulting in less head pressure losses and a more accurate pressure transmission. As a safety feature, construction of the apparatus of the present invention is such that unequal pressure on either side of the membrane diaphragm will cause it to deflect by stretching to the side having lower pressure and it will return back to center on its own when the pressure is relieved. In contrast, the membrane diaphragm of the Gangemi patent unfolds under pressure, does not have a return force, and requires an external force to return it to its original position. The Gangemi construction increases the risk that the membrane will bottom out in use and transmit inaccurate pressure readings.

Therefore, it is an object of the present invention to provide isolating and blood transmitting apparatus that enables a safe, relatively accurate pressure transmission.

A further object of the present invention is to provide an isolating and blood pressure transmitting device that is simple in construction and is easy to manufacture.

Another object of the present invention is to provide isolating and blood transmitting apparatus that is constructed so as to allow a pair of the devices to be placed adjacent to each other with the respective inlets and outlets being located at only a small distance from each other.

A further object of the present invention is to provide an isolating and blood transmitting apparatus that may be produced readily by injection molding.

A further object of the present invention is to provide isolating and blood transmitting apparatus which uses a generally planar membrane that is centered within a pair of generally hemispherical housing members, with the periphery of the membrane being compressed by the housing whereby greater pressure on either side of the membrane will cause it to deflect to the other side by stretching.

Other objects and advantages of the present invention will become apparent as the description proceeds.

BRIEF DESCRIPTION OF THE INVENTION

In accordance with the present invention, an apparatus is provided for isolating a pressure-sensitive device from blood flowing in an extracorporeal blood system and for transmitting the blood pressure from a blood flow line coupled to the pressure sensing device through the isolating apparatus. The apparatus includes a pressure chamber having an inlet coupled to the blood flow line and an outlet coupled to the pressure sensing device. A membrane is disposed transverse the chamber and is surrounded by the chamber to segregate an inlet side of the chamber from an outlet side of the chamber. The membrane is fluid-impermeable and has its outer peripheral portion connected to the surrounding housing.

The improvement comprises a membrane which is a generally planar molded member having a thickness that is less than 0.040 inch and having a diameter that is at least twice as great as the intended total deflection distance. The membrane has a peripheral bead and the housing comprises means for enclosing and compressing the peripheral bead. The membrane is centered within the housing whereby unequal pressure on either side of the membrane will cause it to deflect by stretching to the side having lower pressure.

In the illustrative embodiment, the housing comprises a pair of generally hemispherical members which are complementary to enclose the membrane symmetrically therewithin. The housing has an inlet extending in one direction from the center of one of the members and an outlet extending in an opposite direction from the center of the other member. In the illustrative embodiment, the membrane has a thickness that is about 0.005 inch and has a diameter that is about four times the intended total deflection distance.

A more detailed explanation of the invention is provided in the following description and claims, and is illustrated in the accompanying drawings.

BRIEF DESCRIPTION OF THE DRAWINGS

FIG. 1 is a diagram of a type of blood system to which the present invention is applicable;

FIG. 2 is an elevational view of two isolating devices, constructed in accordance with the principles of the present invention, positioned adjacent to each other;

FIG. 3 is a top plan view of a venous pressure isolator constructed in accordance with the principles of the present invention;

FIG. 4 is a cross-sectional view thereof, taken along the plane of the line 4—4 of FIG. 3;

DETAILED DESCRIPTION OF THE ILLUSTRATIVE EMBODIMENT

Figure 5:
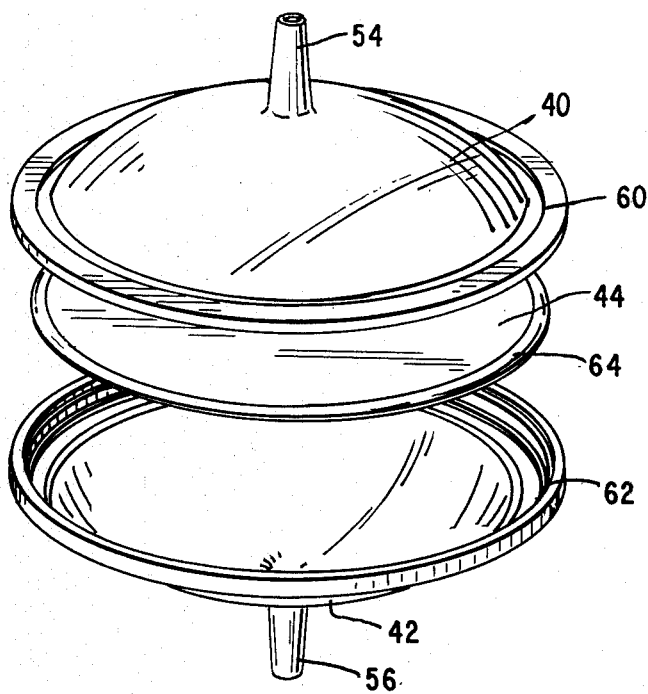
FIG. 5 is an exploded perspective view of a venous pressure isolator constructed in accordance with the principles of the present invention.

Referring to FIG. 1, a diagram of an extracorporeal blood system is shown therein. This system includes an inlet blood line 10 from the patient, through a peristaltic pump 12 and a bubble trap 14 to the blood inlet 16 of a dialyzer 18. A blood outlet 20 is coupled to the dialyzer blood outlet 22 and conveys the blood through bubble trap 24 and back to the patient. Dialysate fluid is pumped to the dialyzer via line 28 and from the dialyzer via line 30.

The blood pressures are measured by a pressure monitor 32 which includes a pressure-sensitive transducer for each blood line under consideration. The pressure-sensitive transducers are isolated from the blood lines by means of blood pressure isolators 34, each of which is coupled between a bubble tube inlet and a pressure-sensitive transducer. One or more outlets 36 from the pressure monitor is utilized to transmit an appropriate signal in connection with the control of the blood flow in the appropriate blood line.

A blood isolating device 34 constructed in accordance with the principles of the present invention is illustrated in FIGS. 2-6. Referring to these figures, isolating device 34 comprises a top half 40 and a bottom half 42 which, when connected together, define a pressure chamber. A membrane diaphragm 44 is disposed transverse the pressure chamber and is surrounded by the chamber to segregate an outlet side 46 (FIG. 4) of the chamber from an inlet side 48 of the chamber.

Top half 40 has a curved internal surface 50 which defines a generally hemispherical segment, while bottom half 42 also has a curved internal surface 52 which also defines a generally hemispherical segment. An outlet 54 is centrally positioned with respect to top half 40 and an inlet 56 is centrally positioned with respect to bottom half 42. Thus outlet 54 and inlet 56 are coaxial.

Figure 6A:
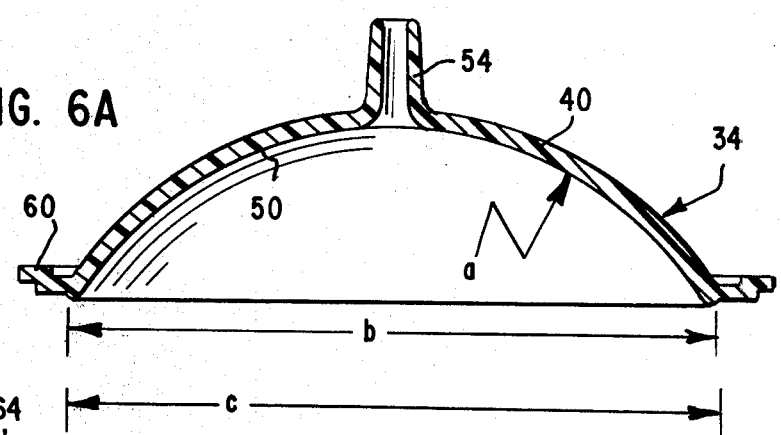
FIGS. 6A, 6B and 6C are exploded cross-sectional views, similar to the cross-sectional view of FIG. 4, with the dimensions of an illustrative example.
Figure 6B:
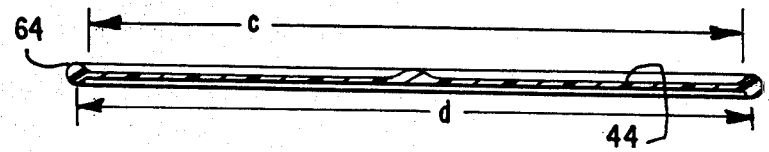
Figure 6C:
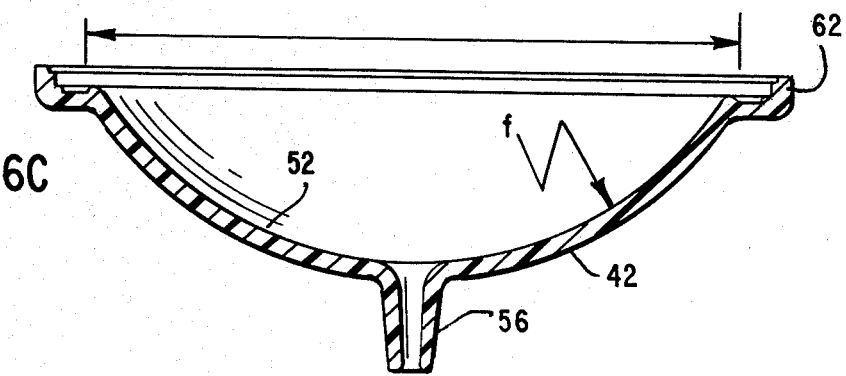

Top half 40 carries a peripheral rim 60 which is illustrated most clearly in FIG. 6A and bottom half 42 carries a complementary peripheral rim 62 which is illustrated most clearly in FIG. 6C. Membrane diaphragm 44 is molded with a peripheral bead 64 which lies within grooves defined by peripheral rim 62 and is enclosed by a complementary engagement with respect to rim 60 and rim 62, as illustrated in FIG. 4. The complementary engagement is such that when rims 60 and 62 are sonic welded together, peripheral bead 64 of membrane 44 will be compressed and held firmly in place.

Membrane 44 with its integral peripheral bead 64 is preferably injection molded of liquid silicone rubber. In an illustrative example, Dow Corning's liquid silicone rubber (Q3-9590) may be used in the injection molding to provide a membrane having extremely low Young's modulus and compression set without requiring a post cure. With Q3-9590 liquid silicone rubber, a Young's modulus of approximately 130 psi and a modulus at 300 percent elongation of approximately 435 psi may be achieved.

The peripheral bead 64 operates as an O-ring to seal the device, to structurally support the membrane and to provide a knock-out area for the part during molding. The liquid silicone rubber material, being liquid, will promote easy mold fill in wide, thin sections.

The membrane is enclosed symmetrically within top half 40 and bottom half 42. Membrane 44 is generally planar and, in order to operate properly, must have a thickness that is less than 0.040 inch and a diameter that is at least twice as great as the intended total deflection distance of the membrane. The Young's modulus of the membrane must not be greater than 300 psi and the modulus at 300 percent elongation must not be greater than 750 psi. As used herein, the term "total deflection distance" connotes the total distance in both directions of the intended deflection of the membrane at its central point. The term "generally planar" connotes a membrane that is substantially flat or is substantially flat with an expanded gate area in the center resulting from injection molding as illustrated in the drawings in which membrane 44 has a central area 66 in which material was allowed to flow to assist injection.

An illustrative example of dimensions which have been found satisfactory are as follows, with reference to FIGS. 6A, 6B and 6C. Referring to FIG. 6A, the internal wall 50 of top half 40 has a spherical radius a of 1.332 inch, with the wall thickness of the top half being 0.050 inch and with diameter b being 2.12 inch. The top half may be injection molded of clear, impact resistant acrylic resin, such as Rohm & Haas Plexiglas DR.

Referring to FIG. 6B, dimension c of membrane 44 is 2.184 inch and dimension d is 2.246 inch, with peripheral bead 64 having a diameter of 0.0625 inch.

Referring to FIG. 6C, bottom half 42 has a wall thickness of 0.05 inch with the internal wall having a spherical radius f of 1.332 inch and with diameter e being 2.120 inch. Bottom half 42 is also injection molded of Piexiglas DR.

Membrane 44 which is molded from liquid silicone, has a thickness of 0.005 inch. By injection molding membrane 44 from an addition cured liquid silicone rubber, there will be easy mold fill in thin sections, very low compression and tension set and modulus. The low set assures that the membrane will retain its seal to the housing and will return to its original shape after deformation. The low modulus allows the membrane to stretch with ease and assures accurate pressure readings. By designing the housing diameter substantially wider than the height of the device and shaping it spherically to follow the contour of the stretched membrane, a relatively small deformation of the membrane allows a large pressure change.

In the illustrative embodiment, the volume on each side of the membrane is about 15 cc, thereby allowing the venous pressure isolator to be used with numerous different types of machines. The membrane of the illustrative embodiment has a total deflection distance of 0.5 inch. Thus the ratio of the membrane diameter to total deflection distance is approximately 4 to 1. This has been found to be an excellent ratio in providing proper operating characteristics.

It has also been found that the membrane must be less than 0.040 inch thick and it is preferably less than 0.01 inch thick. The membrane may be molded from liquid silicone rubber or from silicone rubber filled gum compounds such as Dow Corning's HE-26 catalyzed with Cadet's Cadox TS-50 in the ratio of 1.2 parts TS-50 to 100 parts of rubber. The catalyzed HE-26 compound may be compression molded at approximately 250° F. for three minutes and postcured at 300° F. for two hours. The typical Young's modulus of this HE-26 material is approximately 120 psi and the typical modulus at 300 percent elongation is approximately 180 psi.

If lower negative pressure readings are required, the volume of the fluid contained within the inlet side 48 may be increased with respect to the volume contained within the outlet side 46 by varying the relative sizes of the housing portions 42 and 40.

As illustrated in FIG. 2, flexible plastic tubings 70, 72, 74 and 76 are solvent bonded to the respective outlets and inlets of adjacent isolators 34. The isolators 34 are dimensioned so that when they are located adjacent to each other as illustrated, outlet tubes 70 and 72 lie relatively close to each other and inlet tubes 74 and 76 also lie relatively close to each other in order to obtain maximum efficiency of space. In this manner, the ports are close enough for utility with substantially any machine.

The venous pressure isolator of the illustrative embodiment has been found accurate to within 1 percent of actual pressure from −100 millimeters of mercury to +600 millimeters of mercury. In addition, the device is capable of being sterilized with ethylene oxide, and the device may be radiation sterilized if the housing is formed of Phillips Petroleum K-resin. Such sterilization ability renders the device very suitable for medical use.

It is seen that a simple highly effective device has been provided by utilizing a low modulus membrane having a substantially greater diameter than its deflection distance, with the membrane operating by stretching in contrast to prior art apparatus in which the membrane operates by unfolding. Although an illustrative embodiment of the invention has been shown and described, it is to be understood that various modifications and substitutions may be made by those skilled in the art without departing from the novel spirit and scope of the present invention.

What is claimed is:

1. Apparatus for isolating a pressure-sensitive device from blood flowing in an extracorporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate an inlet side of said chamber from an outlet side of said chamber, said membrane being fluid-impermeable and having its outer peripheral portion connected to the surrounding housing, comprising:
said membrane comprising a generally planar member having a thickness that is less than 0.04 inch and having a diameter that is at least twice as great as the intended total deflection distance; the membrane having a Young's modulus of no more than 300 psi and having a modulus at 300 percent elongation of no more than 750 psi; the membrane being positioned within the housing whereby greater pressure on either side of the membrane will cause it to deflect to the other side by stretching.

2. Apparatus as described in claim 1, said housing comprising a first generally hemispherical member and a second generally hemispherical member, said first and second members being complementary to enclose the membrane symmetrically therewithin.

3. Apparatus as described in claim 1, said membrane having a thickness that is less than 0.010 inch and having a diameter that is about four times the intended total deflection distance.

4. Apparatus as described in claim 3, said membrane having a thickness of about 0.005 inch, a diameter of about two inches and a total intended deflection distance of about 0.5 inch.

5. Apparatus as described in claim 4, wherein said membrane comprises liquid silicone rubber.

6. Apparatus as described in claim 2, each of said generally hemispherical members defining a volume on each side of the membrane of about 15 cc.

7. Apparatus as described in claim 2, said housing having an inlet extending in one direction from the center of said first member and an outlet extending in an opposite direction from the center of said second member.

8. Apparatus for isolating a pressure-sensitive device from blood flowing in an extracorporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate and inlet side of said chamber from an outlet side of said chamber, said membrane being fluid-impermeable and having its outer peripheral portion connected to the surrounding housing, comprising:
said membrane comprising a generally planar molded member having a thickness that is less than 0.040 inch and having a diameter that is at least twice as great as the intended total deflection distance; the membrane having a peripheral bead and the housing including means for enclosing and compressing the peripheral bead; the membrane having Young's modulus of no more than 300 psi and having a modulus at 300 percent elongation of no more than 750 psi; the membrane being centered within the housing whereby greater pressure on either side of the membrane will cause it to deflect to the other side by stretching.

9. Apparatus for isolating a pressure-sensitive device from blood flowing in an extracorporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate an inlet side of said chamber from an outlet side of said chamber, said membrane being fluid-impermeable and having its outer peripheral portion connected to the surrounding housing, comprising:
said housing comprising a first generally hemispherical member and a second generally hemispherical member, said first and second members being complementary to enclose the membrane symmetrically therewithin;
said membrane comprising a generally planar molded member having a thickness that is less than 0.01 inch and having a diameter that is at least twice as great as the intended total deflection distance; said membrane having a peripheral bead; said housing comprising means for enclosing and compressing said peripheral bead; said membrane having Young's modulus of no more than 300 psi and having a modulus at 300 percent elongation of no more than 750 psi; said membrane being centered within the housing whereby greater pressure on either side of the membrane will cause it to deflect to the other side by stretching; said housing having an inlet extending in one direction from the center of said first member and an outlet extending in an opposite direction from the center of said second member.

10. In a method for manufacturing apparatus for isolating a pressure-sensitive device from blood flowing in an extracorporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate an inlet side of said chamber from an outlet side of said chamber, said membrane being fluid-impermeable and having its outer peripheral portion connected to the surrounding housing, the method comprising the steps of:

providing a first housing member;
providing a second housing member;
injection molding a membrane diaphragm from liquid rubber having a Young's modulus of no more than 300 psi and having a modulus at 300 percent elongation of no more than 750 psi;
said membrane being generally planar and having a thickness that is less than 0.04 inch; and
joining the first and second housing members with the membrane diaphragm interposed therebetween.

* * * * *